(12) United States Patent
Waschkies

(10) Patent No.: US 7,373,822 B2
(45) Date of Patent: May 20, 2008

(54) METHOD FOR EVALUATING A WELD JOINT FORMED DURING A WELDING PROCESS

(75) Inventor: Eckhard Waschkies, incapacitated, Blieskastel (DE); by Brigitte Waschkies, legal representative, Blieskastel (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 10/540,210

(22) PCT Filed: Dec. 11, 2003

(86) PCT No.: PCT/EP03/14094

§ 371 (c)(1),
(2), (4) Date: May 26, 2006

(87) PCT Pub. No.: WO2004/054749

PCT Pub. Date: Jul. 1, 2004

(65) Prior Publication Data

US 2006/0260403 A1 Nov. 23, 2006

(30) Foreign Application Priority Data

Dec. 18, 2002 (DE) ............................... 102 59 181
Mar. 20, 2003 (DE) ............................... 103 12 459

(51) Int. Cl.
*G01N 29/04* (2006.01)
(52) U.S. Cl. .......................................... 73/597; 73/602
(58) Field of Classification Search .......... 73/596–600, 73/602, 611, 1.82, 1.86, 614, 618, 622–628; 219/109, 506
See application file for complete search history.

(56) References Cited

U.S. PATENT DOCUMENTS

| | | | | |
|---|---|---|---|---|
| 3,685,348 A | * | 8/1972 | Bottcher et al. | ............... 73/628 |
| 3,739,628 A | * | 6/1973 | Saglio | ........................ 73/627 |
| 3,868,847 A | * | 3/1975 | Gunkel | ........................ 73/622 |
| 4,481,822 A | * | 11/1984 | Kubota et al. | ................ 73/625 |
| 4,481,824 A | * | 11/1984 | Fujimoto et al. | ............. 73/643 |
| 4,588,873 A | * | 5/1986 | Fenn et al. | ............ 219/124.34 |

(Continued)

FOREIGN PATENT DOCUMENTS

DE 4325878 * 2/1994

(Continued)

*Primary Examiner*—Helen Kwok
(74) *Attorney, Agent, or Firm*—Buchanan Ingersoll & Rooney PC

(57) ABSTRACT

A method for evaluating, during a welding process, a welded joint as it is forming between at least two parts of a joint using at least one ultrasonic transmitter sound penetrating the region of the forming welded joint with ultrasonic waves and at least one ultrasonic receiver, which registers the changes in sound transmittance of the ultrasonic waves penetrating the region of the forming welded joint in order to evaluate the welded joint. Sound is transmitted with longitudinal (l) and transverse (t) ultrasonic waves into the region of the welded joint, the time-dependent changes in sound transmittance $D_l(t)$, $D_t(t)$ of the longitudinal ultrasonic waves (l) and the transverse ultrasonic waves (t) being registered separately, and using the ratio of $D_l(t)$ to $D_t(t)$, the time point $t_s$ at which a molten mass forms in the region of the welded joint being determined and serving as a basis for evaluating the welded joint.

9 Claims, 3 Drawing Sheets

U.S. PATENT DOCUMENTS 5,537,876 A * 7/1996 Davidson et al. ............. 73/624
5,920,014 A * 7/1999 Waschkies ................... 73/597
6,250,163 B1 * 6/2001 MacLauchlan et al. ....... 73/643
6,535,828 B1 * 3/2003 Furukawa et al. ............ 702/56
6,640,632 B1 * 11/2003 Hatanaka et al. ............. 73/598
7,004,370 B2 * 2/2006 Arndt et al. ................... 228/8
7,036,376 B2 * 5/2006 Arndt .......................... 73/599

FOREIGN PATENT DOCUMENTS

EP 0132187 * 1/1985

* cited by examiner

METHOD FOR EVALUATING A WELD JOINT FORMED DURING A WELDING PROCESS

TECHNICAL FIELD

The present invention relates to a method for evaluating during a welding process, a welded joint as it is forming between at least two parts of a joint using at least one ultrasonic transmitter, which transmitts ultrasonic waves through the area where the welded joint is forming, and using at least one ultrasonic receiver, which registers the changes in sound transmittance of the ultrasonic waves penetrating the area where the welded joint is forming for evaluation thereof.

PRIOR ART

Generic methods for evaluating welded joints using prior art ultrasonic methods have been common knowledge for some time and are employed to check the quality of welded joints produced in such a manner, usually between two metallic parts of a joint. In addition to prior art subsequent sound transmission of already finished welded joints, DE 43 25 878 C2, for example, describes a on-line evaluating process with which the welding procedures, in particular within the scope of a resistance welding process, can be measured and correspondingly evaluated during the welding process itself. Fur this purpose, the point in time at which the melting temperature of the welding deposit is reached and the welding spot begins to form between the two parts of a joint is determined based on sound transmission and evaluation of transverse ultrasonic waves through the region of the welded joint. The volume of the welding spot is calculated after reaching the melting temperature during the subsequent welding procedure from the weakening of the shear waves, respectively of the transverse waves. Moreover, reference is also made to the preceding document for further comprehensive discussion of the other generic prior art relating to evaluation methods for assessing welded joints.

Figure 2:
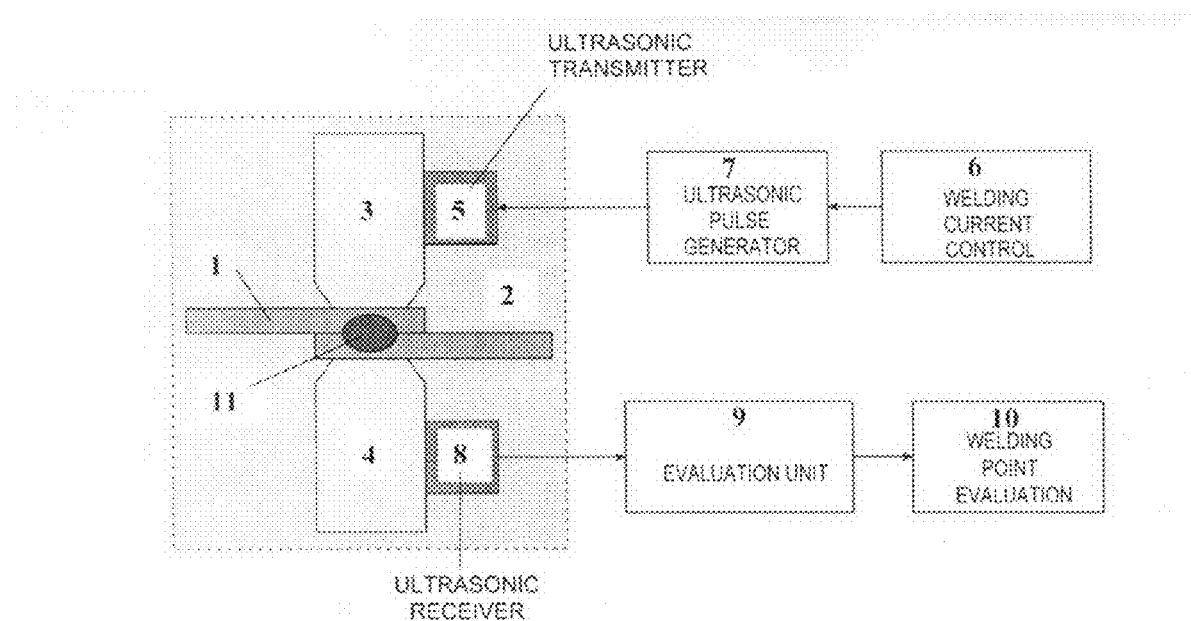

In order to describe the problems involved in the prior art evaluation methods, refer to FIG. 2 herein which shows a standard measuring arrangement for conducting a welding process to join two metal sheet components by means of resistance welding, in which two parts of a joint 1 and 2 designed as flat metal sheets are brought to at least partially overlap in such a manner that they form in the overlapping area a two-layered metal sheet buildup. One welding electrode 3,4, respectively, is placed on opposite sides of the metal sheet buildup. The welding electrodes 3,4 are in contact with the respective part of a joint 1,2 via a preferably plane or crowned contact area. Moreover, in the representation according to FIG. 2, the upper welding electrode 3 is coupled to an ultrasonic transmitter 5, which is triggered via a welding current control 6 connected to an ultrasonic pulse generator 7. In a similar manner, the lower welding electrode 4 is coupled to an ultrasonic receiver 8 whose receiving signals are used via an evaluation unit 9 as a basis for welding point evaluation 10.

The resistance welding process generally comprises three phases. The first phase corresponds to the so-called rate time during which no current flows, the welding electrodes 3,4 however usually press against the parts of a joint 1,2 via the contact areas with an electrode force of 1 to 4 kN. The rate time is followed by the current flow phase or current time in which the parts of a joint are heated until a molten mass in the form of a welding spot 11 forms at least in the contact area between the two parts of the joint 1 and 2. The size of the forming welding spot volume can be adjusted by the strength of the current and the duration of the current flow phase. Finally, the current flow phase is followed by the effective time, respectively the cooling phase, in which the welding spot is cooled until it sets. It is not until the welding spot has set that the welding electrodes open and release the welded joint. Usually, the aforedescribed three phases are selected equally long.

With the aid of the measuring arrangement shown in FIG. 2, sound is transmitted through the region where the welded joint is forming during the welding process itself via the welding electrodes 3,4. For this purpose, transverse ultrasonic pulses are transmitted into the welding electrodes 4 according to FIG. 2. The ultrasonic pulses first pass the welding electrode 3 and then the region where the welded joint is forming until they are finally received by the ultrasonic receiver 8 via the counter electrode 4.

The temporal course of the transverse ultrasonic transmittance through the region of the forming welded joint is utilized to determine the size of the welding spot forming between the parts of the joint 1 and 2 during the current flow phase. When evaluating, it is assumed in the prior art manner that the ultrasonic transmittance behavior of the transverse ultrasonic waves through the forming welded joint region is basically influenced solely by the welding spot formation.

Closer investigation by the applicant, however, has shown that this prior art assumption does not describe the reality of actual ultrasonic wave propagation behavior, in particular of transverse waves, adequately. Consequently, hitherto information about the spatial formation of a welding spot which determines the solidity of a welded joint is not sufficiently precise. For instance, more detailed analyses of sound propagation revealed that ultrasonic transmittance of the parts to be welded together is influenced not only by the formation of the welding spot itself but also by the heating and the enlargement of the contact zones between the respective welding electrodes and the surfaces of the parts of the joint as well as by the contact zones between the respective parts of a joint. It was proven that ultrasonic transmission at the contact zones is strongly dependent on the temperature, the pressure, the frequency and the real size of the contact area. The preceding parameters change during the welding process and exercise considerable influence on the to-be-determined ultrasonic transmittance.

Figure 3:
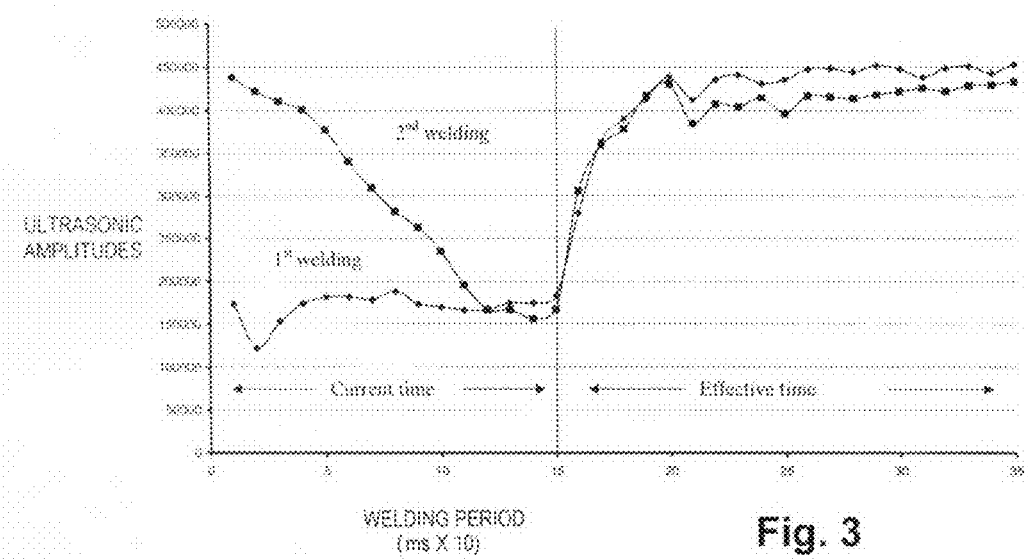

For description of these effects regarding the influence of temperature and the enlargement of the contact area on ultrasonic transmittance through a forming welded joint that has hitherto been neglected in the prior art, refer to FIG. 3.

FIG. 3 shows a diagrammatic representation of the course of the ultrasonic transmittance through a 1 mm thick single metal sheet treated by means of resistance welding twice in succession at the same site. The diagram shows an abscissa along which the welding period is plotted in milliseconds× 10. Shown is only the current flow phase, respectively the current time, of 0 to 150 ms and the cooling phase of between 150 ms and 350 ms. Plotted along the ordinate of the diagram of FIG. 3 are the ultrasonic amplitudes corresponding to the sound transmittance of the ultrasonic waves through the region where the welded joint is forming.

The measured values shown in FIG. 3 correspond to weldings conducted using a current of 5 kA and a respective electrode pressure of 2 kN. The diameter of the contact surfaces between the surface of the metal sheet and the welding electrodes amounts to 4 to 5mm. Subsequent samples of the cooled welded sites prove that no welding spot formed inside the metal sheet.

It was proven that the course of transmittance during the current time does not change much during the first welding (lower functional course within the current time and upper functional course within the effective time/cooling phase). Sound ebbing due to the increase in temperature of the electrode/metal-sheet contacts and the improvement in transmittance due to the increase in the size of the contact areas approximately offset each other. Enlargement of the contact areas does not make itself noticeable until the end of the current time, whereas enlargement of the electrode/metal-sheet contact area leads to a noticeable increase in transmittance during the cooling phase.

If welding is repeated at the same point (strongly diminishing functional course within the current time and the lower functional course within the effective time), the size of the electrode/metal-sheet contact area does not alter significantly as indicated by the fact that the ultrasonic transmittance indicated at the beginning of the current time and at the end of the effective time is practically the same. The diminished transmittance during the current time in the second welding is solely due to the increase in temperature of the electrode/metal-sheet contact. This shows that it is not possible to tell whether sound attenuates due to formation of a liquid phase, respectively due to melting, inside the metal sheet or only due to an increase in temperature at the electrode/metal-sheet contact from the course of sound transmittance, especially in the case of repeated welding. As mentioned in the preceding, to ascertain whether or not complete melting occurring inside the metal sheet is only possible with the aid of subsequent sampling in the region of the welding site.

The above example clearly shows that just examining the sound transmittance behavior of shear waves, respectively of transverse waves, through the welding site does not permit satisfactory ascertainment of the developing welding spot.

SUMMARY OF THE INVENTION

The above makes it clear that it is only inadequately possible, respectively even impossible to evaluate a welded joint as it is forming between two parts of a joint during the welding process using at least one ultrasonic transmitter which transmits ultrasonic waves through the forming welded joint, and at least one ultrasonic receiver, which registers the changes in the ultrasonic waves penetrating the region of the forming welded joint to evaluate the welded joint solely on the basis of solely detecting and evaluating, as such known, transverse ultrasonic waves transmitted through the region of the forming welded joint. Therefore, the object is to provide a method of evaluation which permits informative assessment of a welded joint while avoiding all the inadequacies, respectively uncertainties, inherent in the prior art methods The invented method is based on understanding the necessity to for the most part eliminate the influences on sound transmittance behavior of the contacts between the coupling areas for coupling sound in, respectively coupling it out, at the surfaces of the parts of a joint and between the parts of a joint (until melting starts). As will be described in more detail hereinafter, the invented method permits almost solely determining the melting process in the region of the parts of a joint. For thermodynamic reasons, the melting process usually occurs at the contact zones of the touching parts of a joint.

If melting phases form at other sites, for example the sound coupling-in and coupling-out points, this is also registered and represents a disturbance in the welding process (e.g. failure of the electrodes to cool). It is indicated by the unusual timing of the occurrence of the melting process.

The invented method is based on the following understanding: contacts between solid bodies, such as formed, for example, between the welding electrodes and the surface of one part of a joint and between two parts of a joint lying directly adjacent to each other are by no means ideal perfect contact areas having only little temperature dependency regarding ultrasound transmittance. But rather, such type ultrasonic contacts are imperfect contacts which do possess temperature-based ultrasonic transmittance dependent on contact quality. Contrary to ideal solid body contacts in which the entire area is contacted, real contacts comprise only the sum of the single contacts due to the roughness of the real surfaces. The worse the overall contact, the greater the temperature dependency of the ultrasonic transmittance. A so-called contact stiffness model has been established to describe the sound transmittance through the real interfaces (see J.-M Balk, R. B. Thompson, "Ultrasonic Scattering From Imperfect Interfaces: A Quasi Static Model"; J. Nondestr. Eval. 4 (1984), 177ff; Kendall, K; Tabor, D.: Proc.Roy.Soc. London. A 323, 321 (1971); Peter B. Nagy "Ultrasonic Classification of Imperfect Interfaces" J.NDE, p. 127, vol. 11 1992), according to which ultrasonic transmission at the solid body contacts is only negligibly dependent on the type of wave, i.e. sound transmission of longitudinal and transverse ultrasonic waves through real imperfect contact areas is approximately the same.

In order to determine sound transmittance behavior, for example through a two-layered buildup comprising, for example, two joined layers of metal sheet, it has proven to be possible to describe overall sound transmittances through the metal sheet layers as a product of the sound transmittance through the single sound transmitted zones, i.e. in the case of the preceding two-layered buildup, the product is composed of four single terms, namely transmittance of the electrode/metal-sheet contacts (for coupling sound in and out), transmittance of the metal-sheet/metal-sheet contact and transmittance through the interior of the metal sheet. Finally it can be assumed that liquids, i.e. forming liquid welding spots, are unable to transmit transverse waves, not withstanding that the propagation behavior of longitudinal sound waves are only negligibly influenced by the liquid phase.

Based on the preceding understanding, the invented method is distinguished by longitudinal as well as transverse ultrasonic waves being transmitted through the region of the welded joint. In order to register the two different types of ultrasonic waves, the time-dependent changes in sound transmittance of the longitudinal as well as of the transverse ultrasonic waves, respectively, are registered separately with the aid of the ultrasonic receiver. For selective elimination of contact influences between the sound coupling-in, respectively the sound coupling-out, areas and the respective parts of a joint, the ratio function of the time-dependent sound transmittance changes of the longitudinal and transverse ultrasonic waves is determined. And the time point $t_s$ at which the welded joint forms a molten mass is determined from the obtained ratio function. Both the time point $t_s$ and the further course of the ratio function serve as a basis for evaluating the welded joint.

The invented method is suited not only for examining welded joints, which can be produced by means of a first welding between two parts of a joint, it can also be successfully used in repeated energy application between two or a multiplicity of already united parts of a joint, for example by means of multiple pulse welding. The parts of a joint are already in a first material contact due to the preliminary or first weldings, however this first material contact should be reinforced, respectively solidified, in a monitored manner in a subsequent welding process. Direct monitoring of the forming welding spot permits ascertaining their occurrence, size and thus the quality of the forming welded joint exactly.

The invented method can be utilized independent of the type of welding method. Should there be, in addition to the technical field of application of welding joints, be it contact welding, such as for example resistance welding or noncontact welding, such as for example beam welding, other fields of application in which monitoring the formation of a liquid phase inside a solid medium by means of suited energy input is of significance, e.g. evaluation of melting coatings, the technical teaching of the invented method can also be applied to such cases of application, i.e. the idea on which claim 1 is based should not be limited solely to the welding method per se, but rather should include all those technical applications in which spatially limited molten masses form by means of local thermal heating inside a solid body, for example for local transformation, respectively changing, of the structure of a material. Such type transformations can be utilized, for example, to harden a material locally.

The invented method is described in detail hereinafter with reference to the figures.

BRIEF DESCRIPTION OF THE INVENTION

The present invention is made more apparent, by way of example, without the intention of limiting the scope or spirit of the overall inventive idea using preferred embodiments with reference to the accompanying drawings.

Figure 1A:
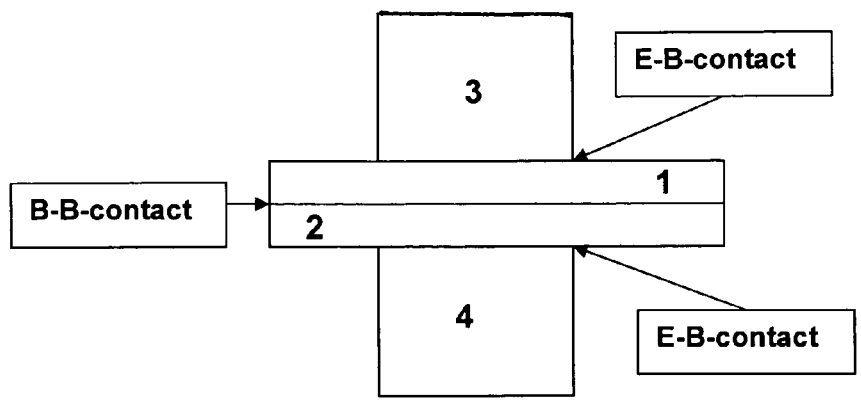
Figure 1B:
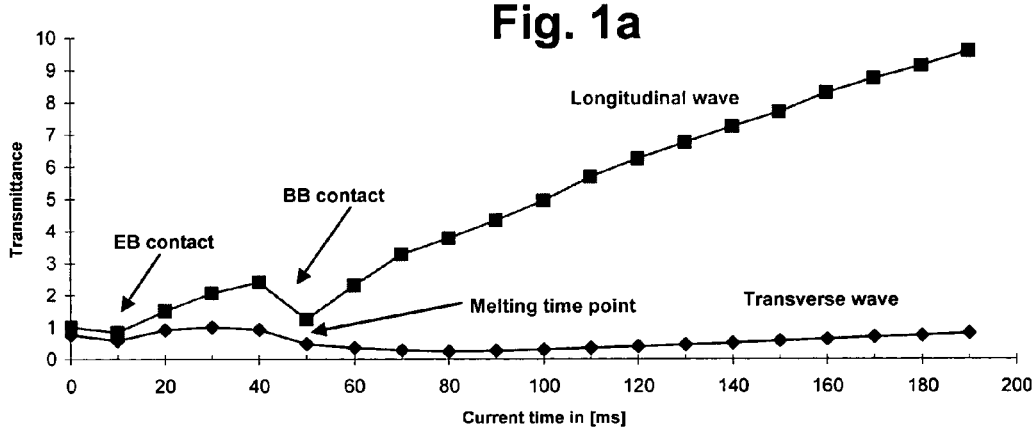
Figure 1C:
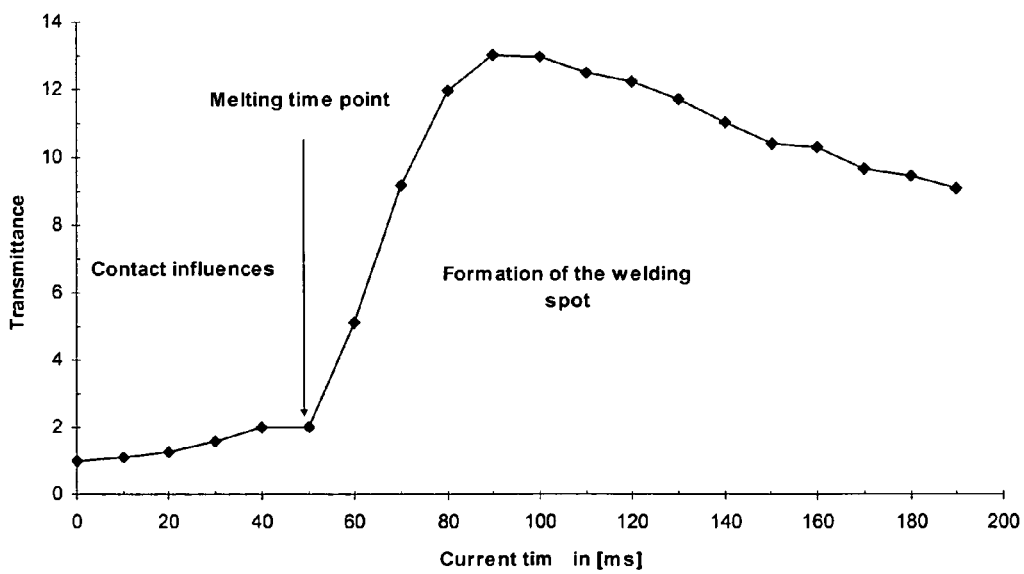
Figure 4:
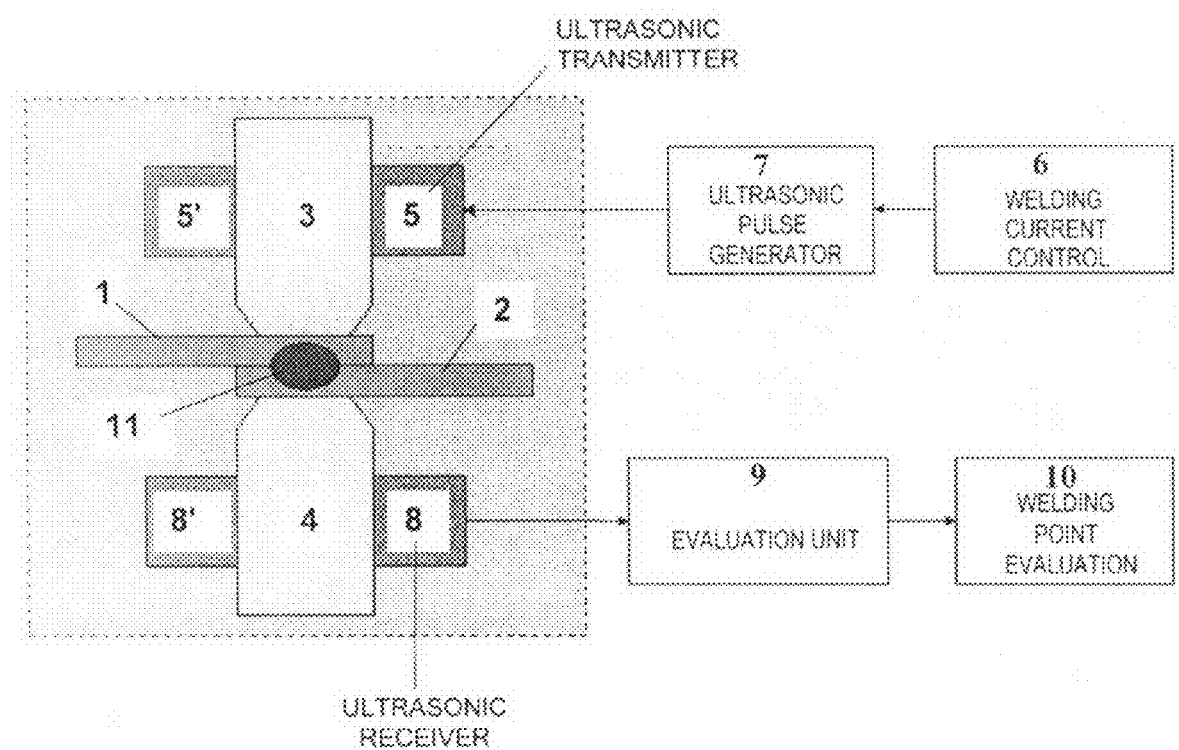

FIG. 1a shows a schematic arrangement for conducting a welding process using resistance welding, FIG. 1b shows a diagrammatic representation to describe the transmittance course of transverse and longitudinal waves and FIG. 1c shows a diagrammatic representation to describe the transmittance course from the ratio of the sound transmittance of the longitudinal wave to the sound transmittance of the transverse wave, FIG. 2 shows a standard arrangement (state of the art), FIG. 3 shows a diagrammatic representation to describe the sound transmittance course of two successive contact weldings conducted on a 1 mm thick metal sheet, and FIG. 4 shows a modified measuring arrangement for separate sound transmittance measurement of longitudinal and transverse waves.

WAYS TO CARRY OUT THE INVENTION, COMMERCIAL APPLICABILITY

For further description of the sound transmittance behavior of longitudinal and transverse waves penetrating a welded joint as it is forming, that is during the welding process, respectively as the waves interact with the welded joint, refer to the very schematic representation in FIG. 1a showing the components that influence the sound path of ultrasonic waves. Thus, it is assumed that two flat metal sheets as parts 1, 2 of a joint are in contact via an areal press contact and form a metal-sheet/metal-sheet contact, B-B contact. For the energy input to form a temperature-dependent welding spot between the two parts 1,2 of the joint, one welding electrode 3,4, respectively, is placed on the corresponding upper sides of the metal sheets forming with the parts 1, 2 of the joint an electrode/metal sheet contact, E-B contact. As already shown with reference to FIG. 2 depicting a standard measuring arrangement for evaluating a welded joint, ultrasonic waves are transmitted via the welding electrodes 3, 4 into, respectively registered in, the parts 1,2 of the joint. Usually an ultrasonic transmitter is coupled to a welding electrode 3 and an ultrasonic receiver is correspondingly acoustically coupled to a welding electrode 4.

Based on the schematic measuring arrangement depicted in FIG. 1a, sound transmittance of longitudinal or transverse waves can be described by the following mathematical relationships:

$$D_l(t) = (EB)_l(t) \cdot (BB)_l(t) \cdot (BI)_l(t) \cdot (BE)_l(t) \quad (1)$$

$$D_t(t) = (EB)_t(t) \cdot (BB)_t(t) \cdot (BI)_t(t) \cdot (BE)_t(t) \quad (2)$$

As already mentioned in the preceding, ultrasonic transmission at solid body contacts, i.e. the real contacts, behaves according to the so-called contact stiffness model according to which ultrasonic transmission is only negligibly dependent on the type of waves, i.e. whether a longitudinal or a transverse wave. On the basis of the preceding mathematical description of the course of transmittance, the sound transmission of the measuring arrangement depicted in FIG. 1a is yielded as products of transmittancies at the individual zones through which sound is transmitted. The terms EB(t), respectively BE(t), stand for the sound transmittance between the electrode/metal-sheet contact occurring at the interface between the welding electrode 3 and part 1 of the joint, respectively between part 2 of the joint and the welding electrode 4. Furthermore, it can be assumed that EB(t) and BE(t) are approximately the same. The inferior indices i and t of the mathematical equations 1 and 2 indicate the sound transmittance through the individual contacts of longitudinal waves (l), respectively transverse waves (t). The term BB(t) stands for the sound transmittance between the metal-sheet/metal-sheet contact between the two parts 1 and 2 of the joint and finally the term Bl(t) stands for the sound transmittance within the part of the joint 1, respectively 2.

Comparison of the mathematical model for the sound transmittance of longitudinal waves and transverse waves given in the preceding by equations 1 and 2 with the actually measured course of the sound transmittance of the longitudinal waves and transverse waves, which are plotted in the diagrammatic representation according to FIG. 1b, permits drawing the following conclusions:

FIG. 1b shows a diagram along whose abscissa the current time during the welding process is plotted. The measured transmittance values are indicated along the ordinate. As to the two functional courses plotted in the diagram, the lower one corresponds to the transmittance behavior of the transverse waves and the upper one to the transmittance behavior of the longitudinal waves. The measured values shown in FIG. 1b are obtained during a resistance welding process at two uncoated metal sheets, each 1 mm thick.

At the beginning of the welding, there is a slight decrease in sound transmittance, which can be explained by the temperature-based ultrasonic attenuation at the electrode/metal-sheet contact. The directly following gaining in effect enlargement of the electrode/metal-sheet contact area nonetheless raises the transmittance of both types of waves. A distinctly recognizable ultrasonic attenuation of both types of waves, caused by an increase in temperature at the interior metal-sheet/metal-sheet contact, does not occur until after approximately 30 to 40ms. As the metal-sheet/metal-sheet contact area is much larger than the electrode/metal-sheet contact area, the raised temperature effect between the metal-sheet/metal-sheet contact area is much greater than the aforedescribed temperature effect at the electrode/metal-sheet contact areas. Until the time point at which the melting temperature $t_s$ defining the melting time point as of which a melting spot begins to form between the parts 1 and 2 of the joint, it is evident that the sound transmittance behavior of the transverse waves as well as of the longitudinal waves can be described in the same manner. However, upon reaching the melting temperature $t_s$ at the metal-sheet/metal-sheet contact, the courses of transmittance of the longitudinal and the transverse waves differ distinctly. The sound transmittance of the longitudinal waves rises despite almost steadily continuing formation of the melting spot between the two parts of the joint due to the enlargement of the electrode/metal-sheet contact areas. On the other hand, the sound transmittance behavior of the transverse waves shows a deeper lasting ebb, due to the welding spot forming at the metal-sheet/metal-sheet contact, because the transverse waves are unable to penetrate through viscous or even liquid phases. But rather transverse waves are actually reflected at the forming melting spot.

In contrast to this, the forming melting spot actually offsets the contact-based attenuation of the longitudinal wave at the metal-sheet/metal-sheet contact before reaching the melting time point due to the occurrence of an ideal area contact as a consequence of which the longitudinal sound transmittance increases continuously after reaching the melting time point as a result of the spreading of the melting spot.

If the sound transmittance of a longitudinal wave and a transverse wave defined in the equations 1 and 2 are put in ratio to each other, all the influences acting in the same manner on both types of waves are offset, in particular the influences arising from enlargement of the contact area as well as from the increase in temperature in the contact zones. The terms $Bl_l$ and $Bl_t$ are offset as they are approximately the same size at low frequencies and especially if the paths through the parts of the joint are short and therefore do not play a significant role in ultrasonic attenuation, yielding the following additional equation:

$$\frac{D_l(t)}{D_t(t)} = \frac{(EB)_l^2(t) \cdot (BB)_l(t) \cdot (Bl)_l(t)}{(EB)_t^2(t) \cdot (BB)_t(t) \cdot (Bl)_t(t)} \quad (3)$$

The above equation (3) can be put in the following manner in the simplified form of equation (4) comprising only two terms according to the equations (5) and (6).

$$\frac{D_l(t)}{D_t(t)} \approx \frac{(EB)_l^2(t) \cdot (BB)_l(t)}{(EB)_t^2(t) \cdot (BB)_t(t)} = f_1^2(t) \cdot f_2(t) \quad (4)$$

with $$f_1(t) = \frac{EB_l}{EB_t}(t) \quad (5)$$

and $$f_2(t) = \frac{BB_l}{BB_t}(t) \quad (6)$$

The equation (5) describes the course of the sound transmittance ratio at the electrode/metal-sheet contacts, which may change somewhat temporally due to plasticization at the electrode/metal-sheet contact. Equation (6) describes the course of the ratio of the sound transmittances at the metal-sheet/metal-sheet contact. This term given again in equation 6 indicates a great change in the region of the melting point $t_s$. This change is related to the solid/liquid transition. Thus the ratio of longitudinal sound wave transmittance to transverse sound transmittance according to equation (4), particularly in the region of the melting point, is essentially determined by the term according to the equation (6) and contact influences are largely eliminated. Therefore, from equation (4), the solid/liquid transition can be easily determined by a sudden drastic rise. For this refer, in particular, to FIG. 1c depicting a diagram in which the functional course of the equation (4), that is the transmittance course of the ratio of the longitudinal wave transmittance to transverse wave transmittance is shown. Thus, the functional course rises slightly steadily between 0 ms and the melting time point $t_s$, which in the case of FIG. 1b lies at about 50 ms. At the melting time point $t_s$, there is a distinct rise in the functional course, which is reflected in a distinct, drastic change in the rising behavior of the function. Thus the rise of the functional course at the point of the melting time point $t_s$ undergoes a considerable positive change determined by the temporal behavior of the term according to equation (6).

The invented division of the sound transmittance behavior regarding the longitudinal and transverse ultrasonic wave parts succeeds in practically completely eliminating the contact influences, caused by the EB and BB contact sites, in evaluating the sonic irradiation behavior of the forming welding point. In many application cases it is significant for the evaluation of a welded joint to simply determine whether or not the liquid phase is reached between the touching parts of the joints during the welding process and if so when. Moreover, the velocity with which the formation of the melting phase occurs is a means of estimating the anticipated size of the welding spot. The velocity with which the welding spot grows is yielded by the rise in the ratio function following the melting time point.

In particular, the invented method broadens possible uses of the ultrasound testing method for evaluating welding points. For example, in the case of several multiple impulse weldings as is described, for example, for the state of the art with reference to FIG. 3, it permits ascertaining exactly whether or not the welding spot has formed, which is not possible with the hitherto ultrasound testing methods as described in the introduction.

In particular, in the case of welding constellations, as for example is the case of microjoints, in which the influence of the contact areas is especially great in comparison to the influence of the liquid phase forming between the parts of the joint, the invented evaluation method permits obtaining reliable information concerning the formation of the liquid phases between the respective parts of the joint.

Moreover, the invented evaluation method opens completely new fields of application in which the influence of the contact zones and of the formation of the liquid phase cannot be separated temporally, as is for example the case in short welding processes, in particular in the case of capacitor discharge welding.

The invented method permits reliable analysis and evaluation of a forming welded joint in which the welding process leads to significant changes in the contact areas at the contact areas between the welding electrodes and the respective parts of the joints, as is the case in so-called projection welding. Such type weldings have hitherto been difficult if not impossible to evaluate.

In a similar manner, the method is suited for assessing weldings of wires on metal sheet or wire on wire. In such cases, too, the contact areas change considerably between the electrodes and the welding part during welding.

In addition to the afore described resistance welding, in which the ultrasonic waves are coupled into the parts of the joint via a welding electrode and coupled out via a correspondingly positioned counter electrode, the invented evaluation process can also be successfully employed in other, in particular, noncontact, welding processes. For example, ultrasonic waves can be coupled into, respectively out of, the to-be-joined parts of the joint in a suited manner by means of a beam welding method, such as for example laser, electron or ion beam processes. However, it is necessary to couple the ultrasonic transmitter, respectively ultrasonic receiver, directly to the corresponding surface of the respective part of the joint. The advantage of the resistance welding method, for example, over noncontact beam welding is that the energy input activating the welding process enters via the same coupling area in the welding part via which the ultrasonic waves for evaluations of the welded joint are also coupled in, respectively coupled out. Nonetheless, the preceding considerations concerning the invented method also find successful use in other types of welding processes.

The invented method principle is fundamentally based on simultaneous determination and evaluation of the longitudinal and transverse transmittance courses through the forming welded joint. Determination of the sound transmittance courses of both types of waves may be realized in various manners. Principally, in sound propagation in spatially limited solid bodies, due to reflection of the sound waves at the boundary areas, the other type wave also occurs, i.e. in the propagation of transverse waves a certain longitudinal part also occurs and vice versa. This part can be influenced by the angle of transmission and the form of propagation medium, in particular when using the invented method in resistance welding, in which the ultrasonic waves are first coupled into the welding electrode.

In addition to the prior art standard measuring arrangement as depicted in FIG. 2, an advantageous measuring arrangement is provided with two ultrasonic transmitters 5,5' according to FIG. 4, of which the one transmitter 5 prefers coupling transverse waves and the other transmitter 5' prefers coupling longitudinal waves into the parts 1,2 of the joint via the welding electrode 3. The counter electrode 4 is also provided with two different receivers 8, 8', of which one ultrasonic receiver is able to detect transverse waves and the other ultrasonic receiver is able to detect longitudinal waves. Working with only one ultrasonic receiver 8 is also feasible. In this case the received signal has to be divided into its longitudinal and transverse parts, which can occur, for example by evaluating the receiving signal in two different time windows.

Evaluation of the receiving signal is also possible in a common time window if the longitudinal and the transverse signal parts lie in different frequency ranges. In such a case, the two vibration parts are selectively detected by corresponding frequency filtering of the receiving signal.

Thus, for example, the measured values shown in FIG. 1a and 1b could be obtained in such a manner, with the receiving signal being received in a broadband manner and then digitally filtered. The transverse receiving signal has been filtered out with a low-pass filter having an upper threshold frequency of 150 kH, the longitudinal receiving signal has been filtered out via a high-pass filter having a lower threshold frequency of 300 kH.

LIST OF REFERENCES 1,2 parts of a joint
3,4 welding electrodes
5,5' ultrasonic transmitter
6 welding current control
7 ultrasonic pulse generator
8,8' ultrasonic receiver
9 evaluation unit
10 welding point evaluation

What is claimed is:

1. A method for evaluating, during a welding process, a welded joint as the welded joint is forming between at least two parts of a joint using at least one ultrasonic transmitter penetrating a region of the forming welded joint with ultrasonic waves and at least one ultrasonic receiver, which registers the changes in sound transmittance of the ultrasonic waves penetrating the region of the forming welded joint in order to evaluate the welded joint, wherein sound is transmitted with longitudinal (l) and transverse (t) ultrasonic waves into the region of the welded joint, the time-dependent changes in sound transmittance $D_l(t)$, $D_t(t)$ of the longitudinal ultrasonic waves (l) and the transverse ultrasonic waves (t) are registered separately, and using a ratio of $D_l(t)$ to $D_t(t)$, the time point $t_s$ at which a molten mass forms in the region of the welded joint is determined and which serves as a basis for evaluating the welded joint.

2. The method according to claim 1, wherein the time point $t_s$ at which a molten mass forms in the region of the welded joint between the parts of the joint is determined by a time point of the time-dependent ratio function of $D_l(t)$ to $D_t(t)$, at which the ratio function indicates a big leap in rising, is determined.

3. The method according to claim 1, wherein the at least one ultrasonic transmitter transmits ultrasonic waves into a first part of a joint via a contact area and the at least one ultrasonic receiver registers ultrasonic waves transmitted into the region of the welded joint via a contact area of a second part of the joint, the following time-dependent ratio function is utilized to evaluate the welded joint:

$$\frac{D_l(t)}{D_t(t)} = \frac{(EB)_l(t) \cdot (BB)_l(t) \cdot (BI)_l(t) \cdot (BE)_l(t)}{(EB)_t(t) \cdot (BB)_t(t) \cdot (BI)_t(t) \cdot (BE)_t(t)}$$

$$\approx \frac{(EB)_l^2(t) \cdot (BB)_l(t)}{(EB)_t^2(t) \cdot (BB)_t(t)}$$

$$\approx \frac{(BB)_l(t)}{(BB)_t(t)}$$

with $(EB)_{l\,or\,t}(t)$≡sound transmittance of longitudinal waves or transverse waves at the sound coupling-in area on the first part of a joint $(BB)_{l\,or\,t}(t)$≡sound transmittance of longitudinal waves or transverse waves at the contact between the parts of a joint $(BI)_{l\,or\,t}(t)$≡sound transmittance of longitudinal waves or transverse waves inside the parts of a joint $(BE)_{l\,or\,t}(t)$≡sound transmittance of longitudinal waves or transverse waves at the sound couplingout area on the second part of a joint with $(BI)^2_{l\,or\,t}(t)$ and $(EB)^2_{l\,or\,t}(t)$ of the longitudinal waves and the transverse waves being largely the same provided that frequencies are low and the transmission paths are short.

4. The method according to claim 3, wherein the evaluation of the welded joint is based on the size of the forming molten mass which is determined from the degree of difference in the rise of the ratio function at the time point $t_s$.

5. The method according to claim 1, wherein the welding is conducted as part of a resistance welding process in which contact electrodes are placed on the parts of the joint, the contact electrodes forming contact areas with the parts of the joint via which the ultrasonic waves are coupled in, respectively coupled out.

6. The method according to claim 1, wherein the welding process is conducted as part of a noncontact welding process in which the ultrasonic transmitter and the ultrasonic receiver are brought in direct contact with the respective part of the joint.

7. The method according to claim 6, wherein laser beam, electron beam or ion beam welding is used as the noncontact welding process.

8. The method according to claim 1, wherein piezoelement probes or EMUS probes are used as the ultrasonic transmitter and the ultrasonic receiver.

9. The method according to claim 1, wherein standard values are generated by means of an online evaluation of the forming welded joint which influence the welding process.

* * * * *